United States Patent [19]

Hebert

[11] 4,452,247

[45] Jun. 5, 1984

[54] HEAT TREATMENT METHOD AND APPARATUS FOR HORSES

[76] Inventor: Dalton Hebert, 3347 SW. 7th St., Ocala, Fla. 32671

[21] Appl. No.: 298,001

[22] Filed: Aug. 31, 1981

[51] Int. Cl.³ .............................................. A61F 7/00
[52] U.S. Cl. ................................... 128/402; 128/400
[58] Field of Search ................. 128/399, 400, 402; 604/312

[56] References Cited

U.S. PATENT DOCUMENTS

| 2,706,988 | 4/1955 | Weber | 128/400 |
| 3,307,554 | 3/1967 | Thornton et al. | 604/312 |
| 3,610,251 | 10/1971 | Sanderson | 128/400 |

FOREIGN PATENT DOCUMENTS

| 1243867 | 9/1960 | France | 604/312 |
| 2247198 | 5/1975 | France | 604/312 |

OTHER PUBLICATIONS

Omaha Vaccine Company, Fall Catalog, p. 91, 1981.

Primary Examiner—C. Fred Rosenbaum
Assistant Examiner—C. W. Shedd

[57] ABSTRACT

A treatment device and method are provided for shaping the neck of a horse. The device comprises an impermeable double-walled sheet made into a sleeve or hood which is proportioned to closely surround the neck of a horse, the sheet providing a space between the walls thereof. A hot air blower is provided and hot air is conducted from the blower into the space between the walls of the sheet at a temperature between about 100° F. and about 175° F. The neck of the horse is caused to sweat and to be shaped as desired.

5 Claims, 3 Drawing Figures

HEAT TREATMENT METHOD AND APPARATUS FOR HORSES

BACKGROUND OF THE INVENTION

In connection with the showing of various breeds of horses, and particularly the Arabian breed, it is desired for the horse to have a neck of particular shape. In the case of the Arabian horses, it is a desirable feature for such horses the have a slim neck. This invention is concerned with the shaping of the neck of the horse to provide these desired features.

There are various prior art devices for humans and animals to provide heat and cold to the body or various parts thereof generally for purposes of relieving pain or alleging to provide certain health features. U.S. Pat. No. 1,338,931 discloses a sweat pad for horse collars adapted to engage the neck of the horse, but this is primarily a padding for the animal. U.S. Pat. No. 3,075,517 discloses a health belt for a human which is adapted to encircle the waist area of a person and contain a liquid in the region of the belt. Liquid flows through the belt and is discharged through ports. U.S. Pat. No. 3,774,617 discloses a treatment device which is particularly adapted to the alleviation of pain through the application of heat or cold. The device, however, is primarily a hot water bottle molded from plastic having a generally horse shoe or U-shaped configuration. U.S. Pat. No. 3,871,381 discloses a cold compress device for the leg of a horse, the compress having a cavity for receiving a compressed refrigerant. U.S. Pat. No. 3,905,367 discloses another device for cooling the leg of a horse which is connectable to a water supply. The device has apertures on the inner face for flowing the water down over the limb of the horse. However, these prior art devices do not teach or disclose how to accomplish the shaping of the horse's neck as provided by the invention herein described.

SUMMARY OF THE INVENTION

According to the invention, a device and method are provided for shaping the neck of a horse by causing the neck to sweat under controlled conditions. The device comprises an impermeable, double-walled sheet which is made into a sleeve or hood proportioned to loosely fit around the neck of a horse. The double-walled sheet provides a hollow space between the walls of the sheet. The sheet is preferably flexible and impermeable on the inner side, but the impermeable outer sheet is provided with vents for discharging hot air or gas from the space. Blowing means are provided for conducting hot air into the space between the walls of the sheet and this hot air flows through the double-walled sheet and out the vents in the outer wall. The temperature of the air or gas is controlled to provide a temperature between about 100° F. and 175° F. in the space. The rate of flow of the gas is adjusted to maintain the inner wall of the sheet warm against the neck of the horse. The device extends from the horse's head at the ears and lower jaw down to the shoulders and back of the horse. Desirably, the lower end of the double-walled sheet is provided with a belt to secure the lower end behind the front legs of the horse.

Various kinds of hot air blowing means can be provided, but it is preferred that the blowing means comprise an economical blower which operates to blow air over a heating element into the space between the walls of the sheet.

The device and method of the invention provide effective shaping of the neck of a horse and is particularly advantageous in respect to shaping the neck of Arabian horses.

DRAWINGS

In the accompanying drawings, the best mode presently contemplated for practicing the invention is shown, in which drawing.

DETAILED DESCRIPTION OF THE ILLUSTRATED EMBODIMENT

Figure 1:
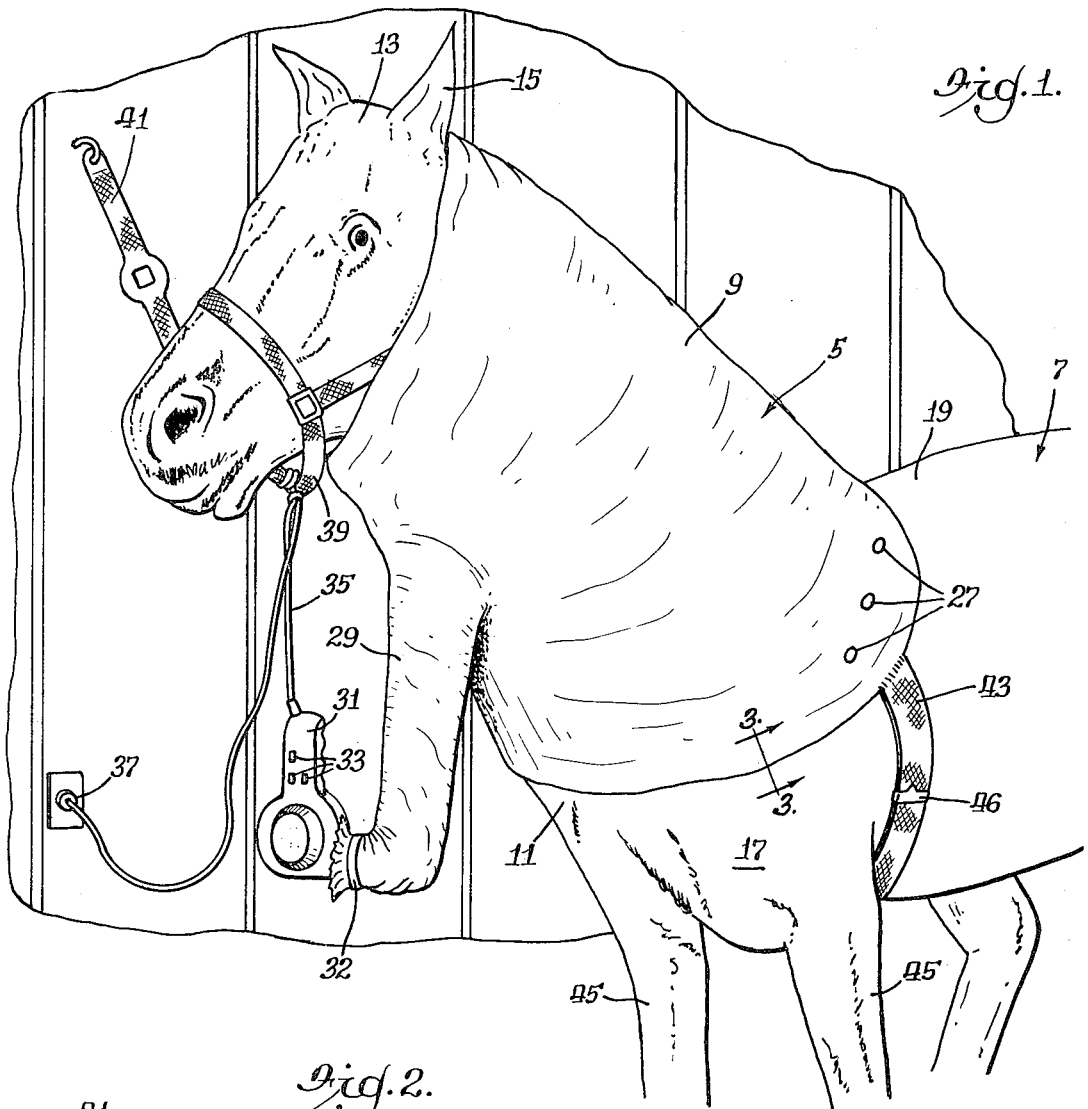
FIG. 1 is a partial perspective view of a horse tethered and provided with the device of the invention.

In the preferred form of the invention illustrated in the drawings, the treament device 5 is shown applied to a horse 7 which is desirably an Arabian horse. The treatment device comprises a generally frusto-conical shaped sleeve 9 made from a flexible double-walled sheet 10 made from a plastic material which is impermeable. The sleeve 9 is proportioned to loosely fit around the neck 11 of the horse 7 and extend down from the head 13 below the ears 15 and lower jaw of the horse. The sleeve 9 terminates at the shoulders 17 and back 19 of the horse.

Figure 3:
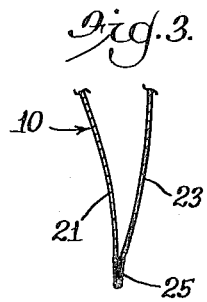
FIG. 3 is a view taken along line 3—3 in FIG. 1 showing the iner and outer walls of the double-walled sheet forming the sleeve and their joinder at the bottom edge of the sheet.

The double-walled sheet 10 forming the sleeve 9 comprises an inner wall 21 and an outer wall 23 (FIG. 3) which are sealed together at the upper and lower edges of the double-walled sheet 10 along seal line 25. The outer wall 23 of the sheet is provided with vents 27 out of which heated air or gas will flow from the space between the inner wall 21 and outer wall 23, as hereinafter pointed out. The outer wall 23, intermediate the upper and lower ends of the sleeve 9 is connected to a tubular section 29. The tubular section or trunk 29 is preferably flexible, and at its lower end is adapted for connection to a hot air blower 31. In this connection, the outer end of the tubular section 29 fits over the discharge end of the blower 31 and a band 32 secures the tubular section 29 to the blower 31. The inner end of the tubular section 29 communicates with the space between the walls 21 and 23 of the sleeve through an opening in the outer wall 23.

The blower 31 is provided with a series of controls 33 adapted to control the rate and temperature of air or gas flow from the blower 31. As shown in the drawings, the hot air blower 31 is electrically powered and connects to a cord 35 which, as shown in the drawings, is plugged into an electrical outlet 37. The drawings illustrate the blowing means 31 being carried by the cord and attached to the bridle 39 on the horse. The horse is tethered to the stall or barn wall by a strap 41.

In the embodiment of the invention illustrated in the drawings, the lower end of the sleeve 9 connects to a belt 43 which extends under the body of the horse behind the front legs 45 in order to hold the treatment device 5 in place at the lower end. A buckle 46 can be provided to readily secure the belt 43 in place.

In operation, the treatment device 5 is fitted over the horse-3 s head with the tubular section 29 extending downwardly, as shown in FIG. 1. The belt 43, if used, is fitted under the body of the horse and buckled into place. Of course, the horse's head should be maintained in a raised position and, for this purpose, the strap 41 is connected to the wall of the stall or barn. The blower 31 is then connected to the tubular section 29 by means of the band 32. As illustrated in the drawings, the blower 31 is held onto the bridle 39 by means of the cord 35. The blower 31 is plugged into the outlet 37 and a desired air flow and temperature are set by means of the controls 33. The air control is blown through the sleeve 9 at a temperature between about 100° F. and 175° F. The air enters the tubular section 29 and goes into the space between the walls 21 and 23 of the sheet 10 and exits by way of the vents 27. The heat provided by the treatment device causes the neck of the horse to sweat and to be shaped. Repeated treatments can be provided to give the desired results.

Figure 2:
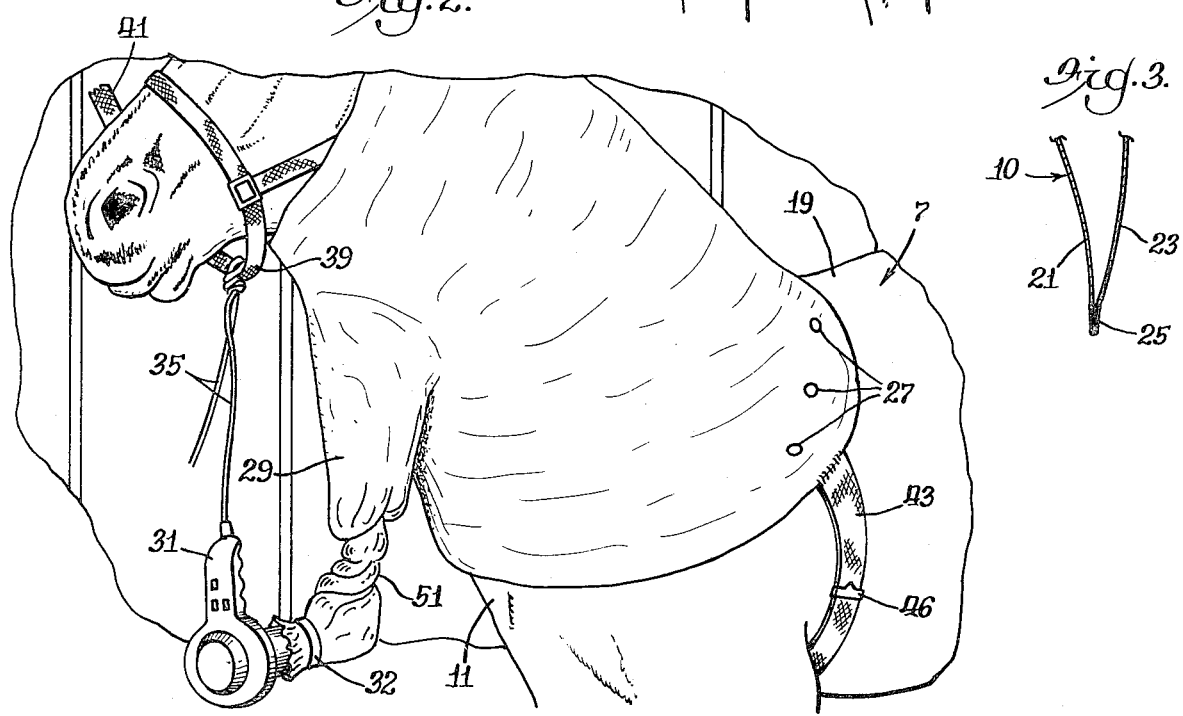
FIG. 2 is a partial view of FIG. 1 showing a condition of the device which should be avoided in the practice of the invention.

FIG. 2 illustrates a condition which is to be avoided in the operation of the treatment device 5 and particularly shows that the tube should not be twisted as illustrated at 51. Such twisting can result in burning out the blowing device 31 and, of course, does not provide the desired operation of the treatment device 5 of the invention.

The various features of the invention which are believed to be new are set forth in the follwing claims:

What is claimed is:

1. A treatment device for shaping the neck of a horse comprising, in combination, a flexible impermeable sleeve formed from a double-walled sheet proportioned to loosely surround the neck of a horse, said sleeve having an upper end which closely fits the upper neck adjacent the ears and lower jaw and having a lower end which closely fits the lower neck adjacent the shoulders and back, said sleeve being generally frusto-conical in shape, said sheet providing a space between the walls thereof, strap means extending downwardly from the lower end of the sleeve for securing said lower end in position adjacent the shoulders and back, hot air blowing means, and means for conducting hot air from the blowing means into said space between the walls of the sheets to transfer heat to the neck of the horse, one wall of said sheet being provided with vent openings spaced from the heat conducting means.

2. A treatment device in accordance with claim 1 wherein said blowing means comprises a fan and heating element and said conducting means comprises a flexible tube connected to said blowing means and communicating with the space between said walls of said double-walled sheet.

3. A treatment device in accordance with claim 2 wherein said blowing means is positioned beneath said sleeve and said flexible tube extends downwardly from said sleeve to said blowing means to provide partial support for said blowing means.

4. A treatment device in accordance with claim 3 further comprising support means for suspending said blowing means from the bridle of the horse so that said blowing means is partially supported by the bridle.

5. A method for shaping the neck of a horse comprising encasing the neck in an impermeable plastic sleeve which includes a wall disposed toward the neck of the horse, constraining the head of the horse, securing the plastic sleeve in place, heating the external side of said wall with flowing heated air, conducting the flowing air from the heated sleeve, and maintaining the temperature of the flowing air between about 100° F. and about 175° F., whereby the neck of the horse is caused to sweat and to be shaped.

* * * * *